(12) United States Patent
Biedermann et al.

(10) Patent No.: US 8,414,621 B2
(45) Date of Patent: Apr. 9, 2013

(54) MODULAR SYSTEM FOR THE STABILIZATION OF THE SPINAL COLUMN

(75) Inventors: Lutz Biedermann, VS-Villingen (DE); Wilfried Matthis, Weisweil (DE); Martin Pabst, Donaueschingen (DE); Berthold Dannecker, St. Georgen (DE)

(73) Assignee: Biedermann Technologies Gmbh & Co. KG, Donaueschingen (DE)

( * ) Notice: Subject to any disclaimer, the term of this patent is extended or adjusted under 35 U.S.C. 154(b) by 635 days.

(21) Appl. No.: 12/540,267

(22) Filed: Aug. 12, 2009

(65) Prior Publication Data

US 2010/0042155 A1    Feb. 18, 2010

Related U.S. Application Data

(60) Provisional application No. 61/088,274, filed on Aug. 12, 2008.

(30) Foreign Application Priority Data

Aug. 12, 2008  (EP) ..................................... 08014379

(51) Int. Cl.
*A61B 17/70* (2006.01)
(52) U.S. Cl. ........................................ 606/264; 606/259
(58) Field of Classification Search .................. 606/246, 606/254–262, 264–279
See application file for complete search history.

(56) References Cited

U.S. PATENT DOCUMENTS

| 6,241,730 | B1 | 6/2001 | Alby |
| 6,296,644 | B1 | 10/2001 | Saurat et al. |
| 6,802,844 | B2 | 10/2004 | Ferree |
| 7,083,621 | B2 | 8/2006 | Shaolian et al. |
| 7,175,622 | B2 | 2/2007 | Farris |
| 8,080,038 | B2 * | 12/2011 | Bhatnagar et al. ............. 606/255 |
| 2005/0038432 | A1 | 2/2005 | Shaolian et al. |
| 2005/0096659 | A1 | 5/2005 | Freudiger |
| 2005/0203518 | A1 | 9/2005 | Biedermann et al. |
| 2007/0123866 | A1 | 5/2007 | Gerbec et al. |
| 2007/0135815 | A1 | 6/2007 | Gerbec et al. |
| 2007/0270821 | A1 | 11/2007 | Trieu et al. |
| 2008/0154308 | A1 * | 6/2008 | Sherman et al. ............. 606/265 |
| 2008/0183214 | A1 | 7/2008 | Copp et al. |

(Continued)

FOREIGN PATENT DOCUMENTS

EP   1 527 742 A1   5/2005
EP   1 757 243 A1   2/2007

(Continued)

OTHER PUBLICATIONS

European Search Report for European Application No. 08014379.5-2310, European search report dated Jan. 9, 2009 and mailed Jan. 20, 2009 (6 pgs.)

*Primary Examiner* — Eduardo C Robert
*Assistant Examiner* — Atiya Mahmud
(74) *Attorney, Agent, or Firm* — Christie, Parker & Hale, LLP

(57) ABSTRACT

A modular system for stabilization the spinal column or other bones includes a first stabilization element, a second stabilization element to be connected to the first stabilization element, and an outer connection element to connect the first stabilization element to the second stabilization element. An end portion of the first stabilization element and an end portion of the second stabilization element each include a structure engaging with a corresponding structure provided in the outer connection element to establish a form-fit connection.

36 Claims, 8 Drawing Sheets

| U.S. PATENT DOCUMENTS | | | | FOREIGN PATENT DOCUMENTS | | |
|---|---|---|---|---|---|---|
| 2008/0215095 A1 | 9/2008 | Biedermann et al. | | WO | WO 2008/021107 A2 | 2/2008 |
| 2008/0234743 A1 | 9/2008 | Marik | | WO | WO 2008/098206 A1 | 8/2008 |
| 2008/0234744 A1* | 9/2008 | Zylber et al. | 606/264 | WO | WO 2008/115622 A1 | 9/2008 |
| 2009/0005817 A1* | 1/2009 | Friedrich et al. | 606/246 | | | |
| 2009/0036924 A1 | 2/2009 | Egli et al. | | | | |

* cited by examiner

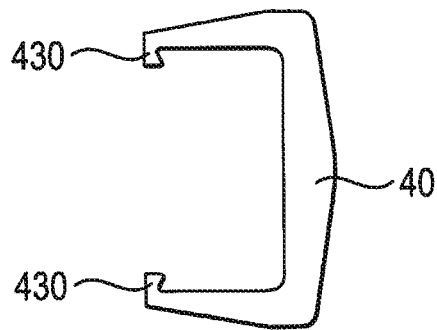
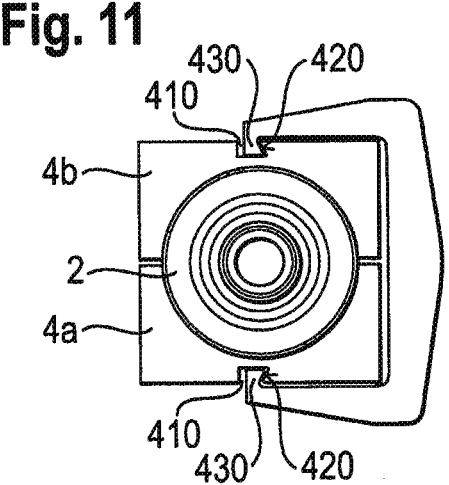
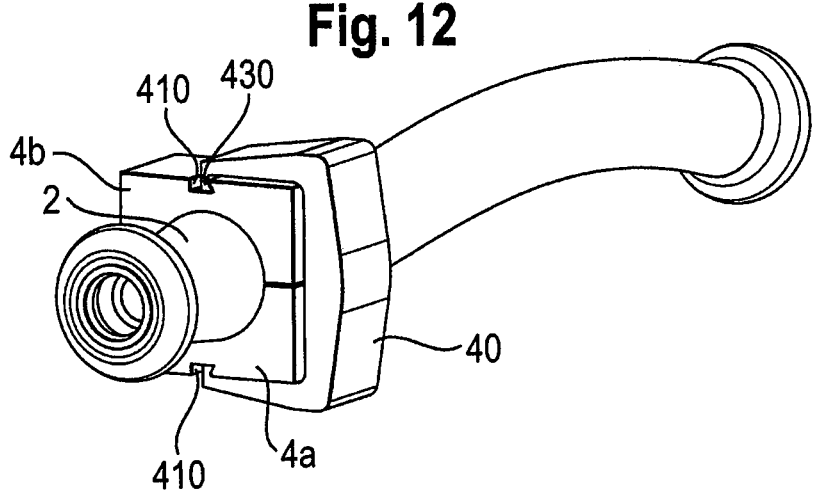

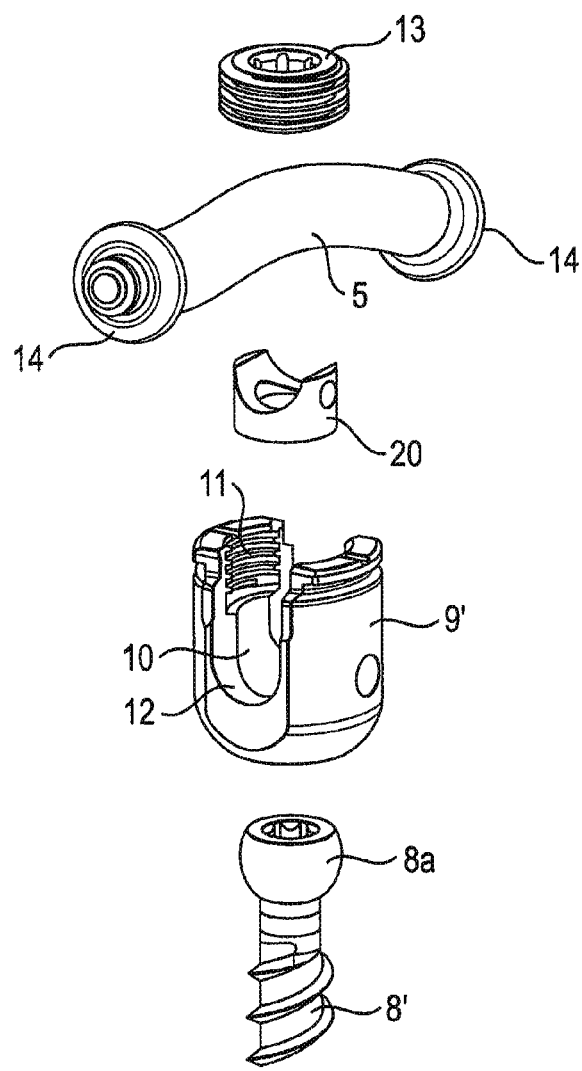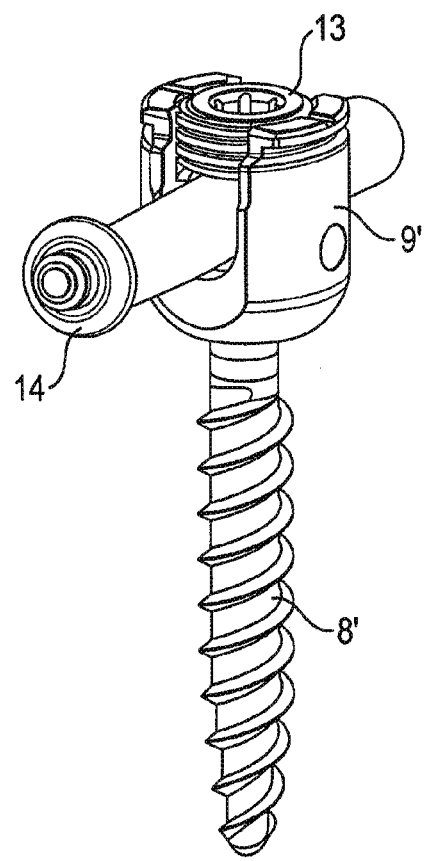

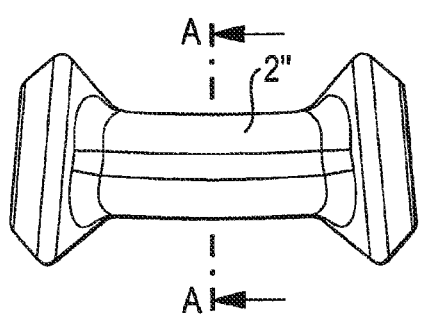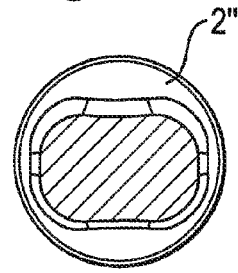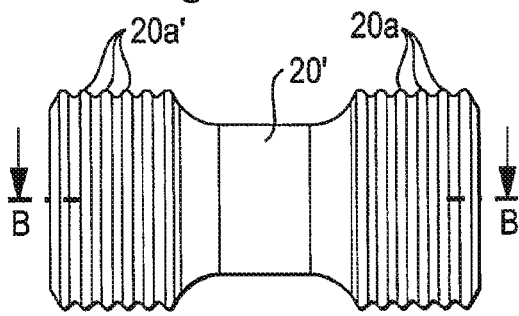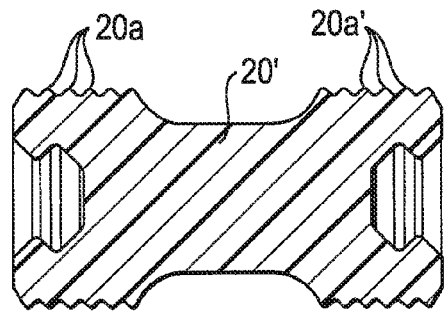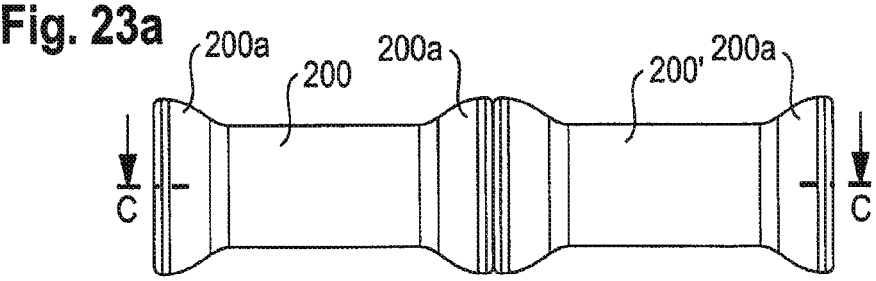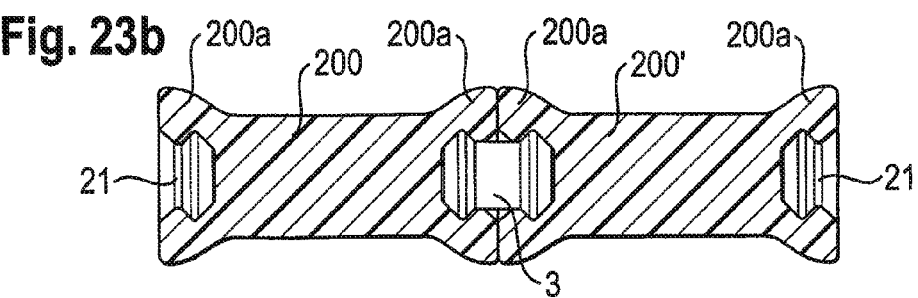

MODULAR SYSTEM FOR THE STABILIZATION OF THE SPINAL COLUMN

CROSS-REFERENCE TO RELATED APPLICATION(S)

The present application claims the benefit of U.S. Provisional Patent Application Ser. No. 61/088,274, filed Aug. 12, 2008, the contents of which are hereby incorporated by reference in their entirety, and claims priority from European Patent Application EP 08 014 379.5, filed Aug. 12, 2008, the contents of which are hereby incorporated by reference in their entirety.

BACKGROUND

The invention relates to a modular system for the stabilization, in particular for the dynamic stabilization, of the spinal column.

A stabilization system including one or more bone screws and a connector for traversing a space between one or more bony structures is known from US 2007/0270821 A1. In one embodiment the connector consists of a sequential connection of elastic and inelastic components, which can be connected to each other, for example, by a threaded connection, a snap-fit connections, a quick-connect connection or other interlocking connections. The flexible connector can be connected to the vertebrae of the spinal column, for example, by pedicle screws.

A rod-shaped implant element for the application in spine surgery or trauma surgery and the stabilization device with such a rod-shaped implant element, which has rigid end portions and a flexible middle portion is known from EP 1 757 243 A1.

EP 1 527 742 A1 describes a closure device for a pedicle screw which fixes a single elastic rod-element in a form-fit manner.

Based on the above, there is a need to provide a modular system for the stabilization of the spinal column, which is adaptable to the individual anatomic conditions and requirements of the patient.

SUMMARY

The system of the disclosure includes a combination of a plurality of rigid and/or flexible stabilization elements which form a rod-like stabilization member and bone anchors to connect the stabilization member to the vertebrae of the spinal column.

The requirements for a stabilization system of the spinal column may be different from one motion segment to another motion segment in terms of the desired rigidity or stability and/or in terms of geometry such as the length of the segment and the angular position of the vertebrae with respect to each other.

The system of the disclosure has the advantage that specific stabilization elements can be combined according to the conditions at the operation site. This can be done, for example, by the surgeon during surgery.

The system of the disclosure allows to combine stabilization elements having different characteristics such as rigid and flexible, different materials or different degrees or orientation of flexibility. The elements can be combined outside the patient's body and after connection of the elements the system can be inserted in bone anchors. Since the elements have a length which is short compared to long elastomer rods extending over several motion segments, the manufacturing of the elements is simplified.

The stabilization elements are fixed in bone anchors, such as pedicle screws, at their respective end portions, which permits to use the largest portion of the flexible elements for flexion or extension. The stabilization elements can also be connected to each other with a connection element at a location between two bone anchors.

BRIEF DESCRIPTION OF THE DRAWINGS

FIG. 10 shows a side view of a locking element for connecting the two halves of the outer connecting element.
FIG. 11 shows a front view of the outer connection element connecting two stabilization elements seen from the end of one stabilization element.
FIG. 12 shows a perspective view of the outer connecting element connecting two stabilization elements.
FIG. 15 shows an exploded perspective view of a single stabilization element together with a polyaxial bone screw.
FIG. 16 shows the system of FIG. 15 in an assembled and fixed state.
FIGS. 21a to 21b show a modification of a stabilization element in a side view and a sectional view along line A-A.
FIGS. 22a to 22b show a further modification of a stabilization element in a side view and in a sectional view along line B-B.
FIGS. 23a to 23b show a still further modification of the stabilization element connected to another stabilization element in a side view and in a sectional view along line C-C.

DETAILED DESCRIPTION

Figure 1:
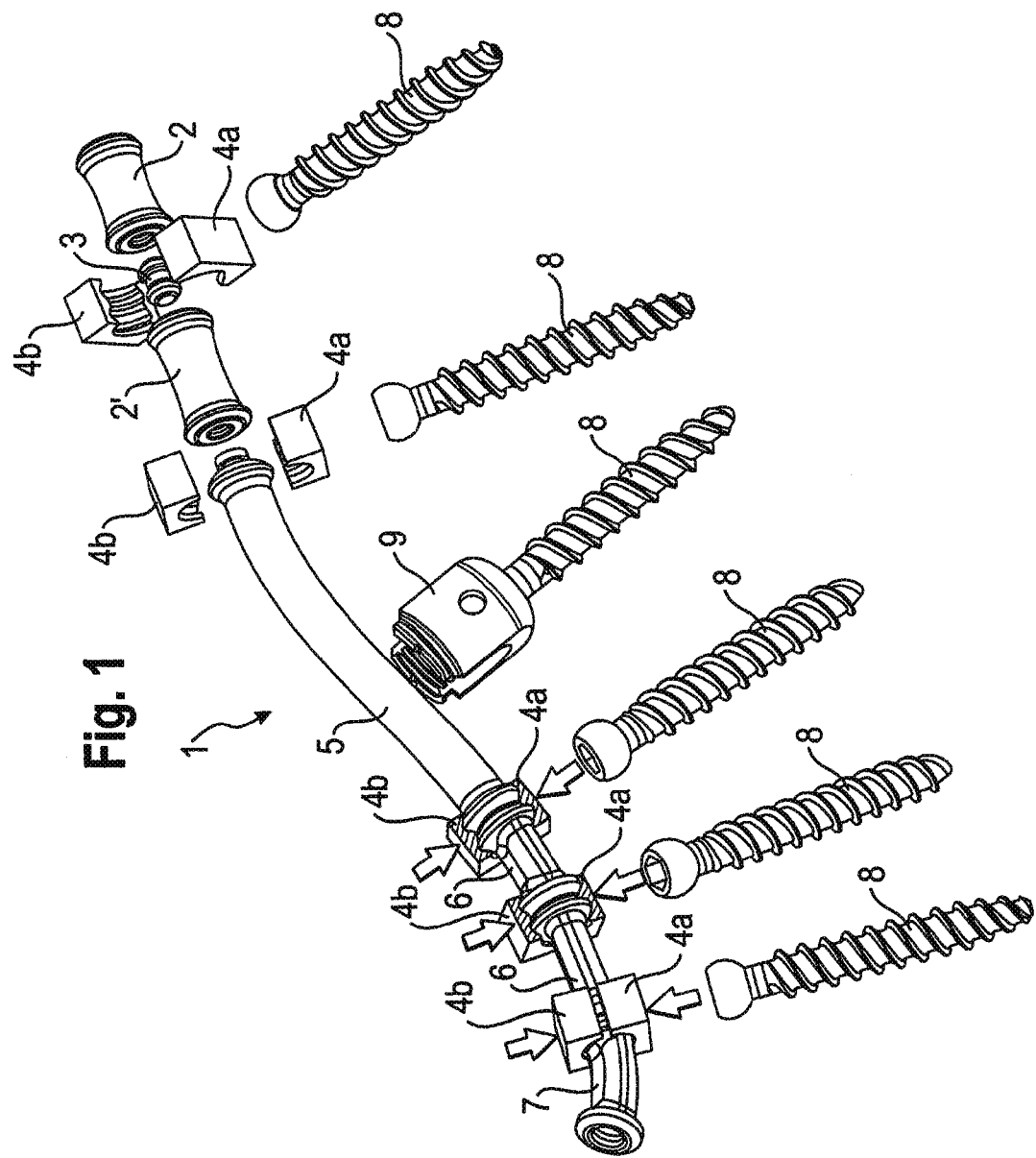
FIG. 1 shows a perspective exploded view of an embodiment of the modular system.

A modular stabilization system according to the disclosure is schematically shown in FIG. 1. The system includes at least two, usually a plurality of rod-like stabilization elements, which may have the same or different properties and/or geometries. For example, the modular stabilization system 1 includes flexible stabilization elements 2, 2', which can be connected by an inner connection element 3, and an outer connection element 4a, 4b. In addition, the modular stabilization system may include a rigid stabilization element 5 which can be connected to a flexible stabilization element 2, 2' by an outer connection element 4a, 4b. The term flexible means that the stabilization element, when implanted in the patient's body, allows a certain degree of flexion and/or extension and/or torsion of the spinal motion segment. The term rigid means that it doesn't allow such a limited motion under normal load conditions of the spinal column. The modular stabilization system 1 can include further rod-like stabilization elements 6, 7, which may differ in length and shape compared to the other stabilization elements. For example, the stabilization elements 6 differ in cross-section from the stabilization elements 2 and 5. The stabilization element 7, in addition, is curved. Each stabilization element is connected to a neighbouring stabilization element via an outer connection element 4a, 4b.

The term rod-like means that the stabilization element has elongate shape and can be received in a receiving part of a bone anchor.

The stabilization system 1 is connected to bone anchors 8 which are to be anchored in vertebrae of the spinal column. As shown with respect to the stabilization element 5, the bone anchor 8 may be a pedicle screw having a receiving part to receive the rod-like stabilization element 5.

Figure 2:
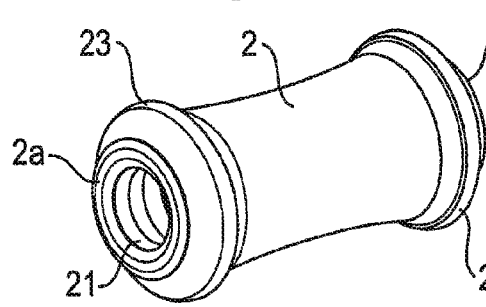
FIG. 2 shows a perspective view of a flexible stabilization element of the system according to one embodiment.
Figure 3:
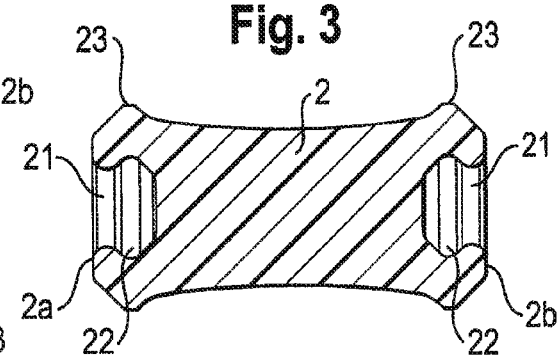
FIG. 3 shows a sectional view along the longitudinal axis of the flexible stabilization element according to FIG. 2.

As can be seen in FIGS. 2 and 3, the flexible stabilization element 2 has a rod-like shape with a first end 2a and a second end 2b and a circular cross-section. At each end a blind hole 21 is provided extending to a distance from the first end 2a and the second end 2b, respectively. The blind hole 21 has a portion 22 forming a circular undercut. The outer diameter of the flexible stabilization element 2 varies over the length of the stabilization element in such a way that at a distance from the first end 2a and the second end 2b corresponding to the position of the undercut 22 a circular rib-like projection 23 is formed. The diameter of the stabilization element 2 further varies in such a way that it decreases slightly towards the middle of the stabilization element in a lengthwise direction.

The flexible stabilization element 2 is made of a material which is flexible under the application of forces arising from the motion of the vertebrae against each other. For example, the material can be an elastomer material, such as polycarbonate urethane (PCU) or polyurethane or polysiloxane. However, any other body compatible materials exhibiting flexibility can be used. The length of the flexible stabilization element is such that usually one motion segment of the spine can be bridged by the flexible stabilization element. Hence, the stabilization system may comprise a plurality of flexible stabilization elements 2 of different length to apply it to different locations of the spine. Also, the diameters of such flexible stabilization elements may vary to provide the desired characteristic for stabilization. The end portions having the rib-like projections should have the same size in order to allow the flexible stabilization elements to be connected to a neighbouring stabilization element via the outer connection elements described hereinafter.

Figure 4:
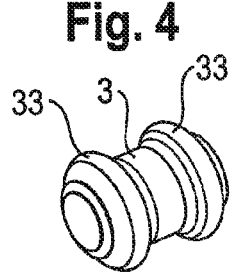
FIG. 4 shows a perspective view of an inner connection element for connecting two flexible stabilization elements according to FIG. 2.
Figure 5:
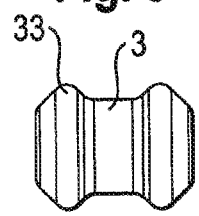
FIG. 5 shows a side view of the inner connection element of FIG. 4.
Figure 6:
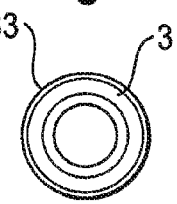
FIG. 6 shows a front view of the inner connection element of FIG. 4.

FIGS. 4-6 show the inner connection element 3, which is adapted to connect two of the flexible stabilization elements 2. The inner connection element is made of a rigid material, such as metal, in particular a body-compatible metal such as titanium, stainless steel or body-compatible alloys or of a rigid plastic material, such as PEEK or others. The shape of the inner connection element 3 is approximately bar-bell-shaped. In particular, it has at a distance of each end a circular rib-like projection 33 which is shaped so as to fit into the undercut portion 22 of the blind hole 21 of the flexible stabilization element 2 as shown, for example, in FIG. 18. Hence, the inner connection element 3 can be inserted in the blind hole 21 of one flexible stabilization element 2 by pressing or snapping it into the bore which is possible due to the flexibility of the flexible stabilization element 2. For connection to the second flexible stabilization element 2' it can be pressed into the blind hole 21 of the second flexible stabilization element.

Connected in this way, the stabilization system includes two flexible stabilization elements 2, which are adapted to bridge two motion segments of the spine. The connection is established with a form-fit (also called positive fit) connection between the inner connection element 3 and the undercut portion 22 of the blind hole 21 of the flexible stabilization element 2.

Figure 7:
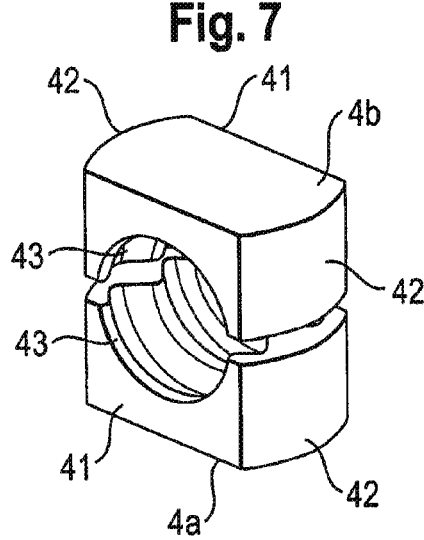
FIG. 7 shows an embodiment of an outer connection element for connecting two stabilization elements of the system.
Figure 8:
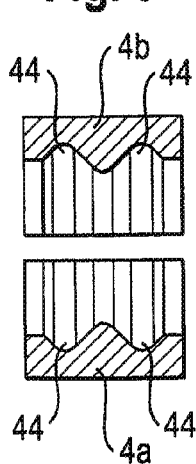
FIG. 8 shows a sectional view along the cylinder axis of the outer connection element of FIG. 7.
Figure 9:
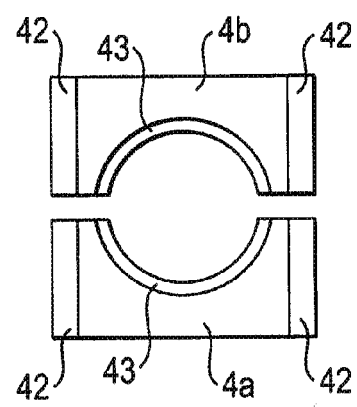
FIG. 9 shows a front view of the connection element of FIG. 7.

The outer connection element according to FIGS. 7-9 includes two identical halves 4a, 4b which are approximately rectangular in shape with two long sidewalls 41 and two short side walls 42 connecting the long side walls. The short side walls 42 are outwardly curved. The curvature serves for allowing the outer connection element to be introduced in a receiving portion of a bone anchor and to be moved therein. Each of the outer connection elements 4a, 4b includes a cylinder segment-shaped recess 43 with two circular grooves 44 the size and shape of which is designed so as to fit on the circular rib-like projections 23 of the flexible stabilization element 2. When the flexible stabilization element 2 is connected to another flexible stabilization element 2' via the inner connection element 3, the outer connection element 4a, 4b engages the connection site in a form-fit manner.

The two halves 4a, 4b of the outer connection element may be connected outside the receiving portion of a bone anchor. As shown in FIGS. 10 to 12 an elastic clamp 40 can be used for connecting the two halves 4a, 4b. To accomplish such a connection, the portions 4a,4b of the outer connecting element have on their faces which are opposite to the stabilization elements, grooves 410 which may have an undercut portion 420 in which a catch portion 430 of the clamp 40 engages. The clamp 40 can be easily snapped onto the outer connection element which encompasses the stabilization elements. The outer connection element thereby firmly connects the stabilization elements pressure and form-fit connection. Other way for connecting the two portions of the outer connecting element are conceivable, such as screw connections, other kinds of snap fit connections or any other methods and devices.

The function of the connection between the stabilizing elements and the outer and inner connecting element is as follows. The inner connection element 3 connects the two stabilization elements with a form-fit connection. Thereby, a holding force is established which provides a preliminary fixation. The outer connection element 4a, 4b provides an additional holding force with a form-fit connection since the rib-like projections of the stabilization element engage in the grooves of the connection element. In the receiving portion of the bone anchor pressure is exerted (shown by the arrows in FIG. 1) which presses the halves 4a, 4b against the stabilization elements. Hence, the final connection is established by a combination of form fit and frictional fit. The inner connection element 3 prevents a deformation of the flexible stabilization element. As a consequence, the holding force is increased.

Figure 13:
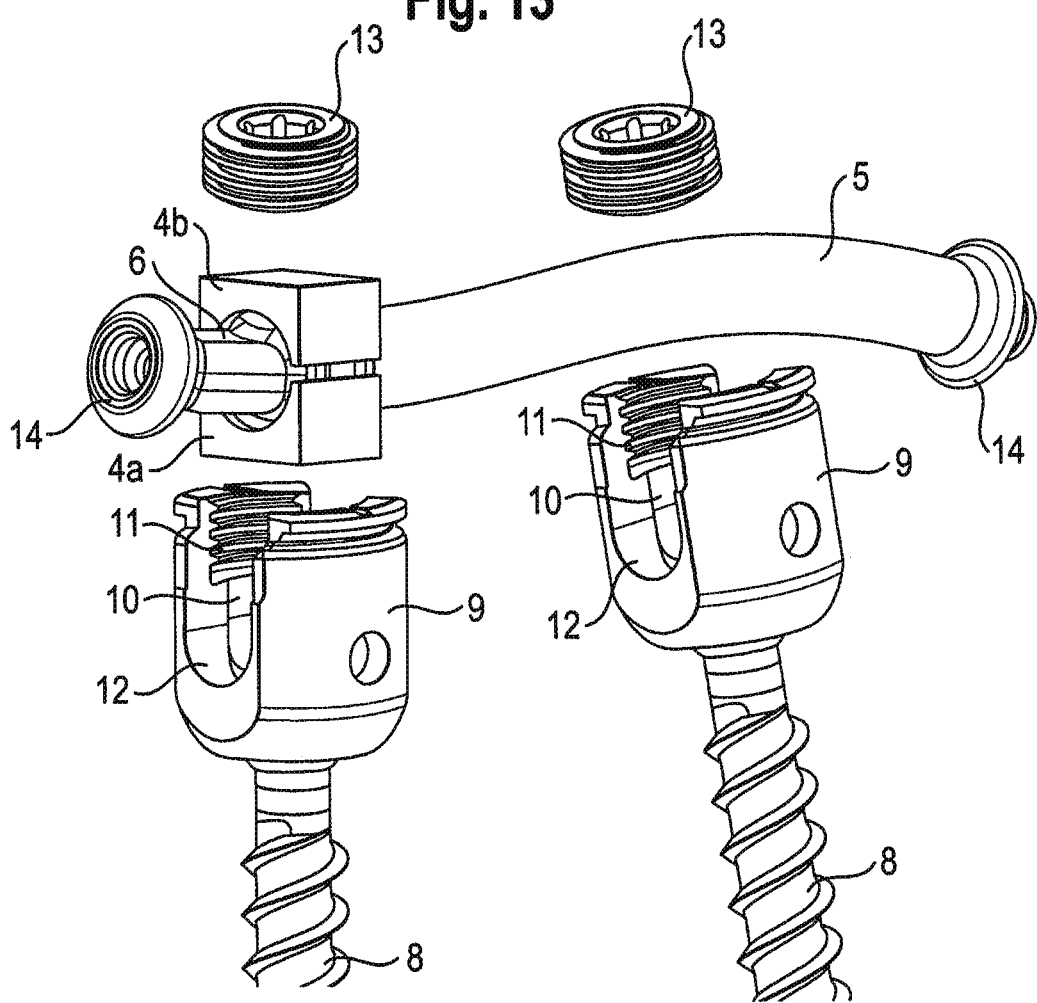
FIG. 13 shows an enlarged perspective view of the stabilization system with two different stabilization elements and two bone anchors
Figure 14:
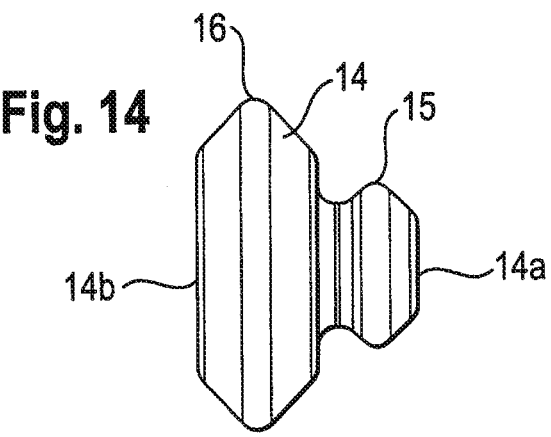
FIG. 14 shows a side view of a further connection element.

FIGS. 13 and 14 show a connection of the stabilization system to the bone anchor 8. The bone anchor 8 includes a threaded shaft and a receiving portion 9. The receiving portion 9 is substantially cylindrically-shaped and includes a coaxial bore 10 with an internal thread 11 at the open end and a substantially U-shaped recess 12 for receiving the stabilization element. As shown particularly in FIG. 13, the outer connection element 4a, 4b is designed such as to be insertable from the open end into the receiving portion 9 and to be moved therein in an axial direction. An inner screw 13 is provided to be screwed in into the receiving portion and to exert pressure on the upper half 4b of the outer connection element. The pressure exerted by the inner screw presses the upper half 4b of the outer connection element against the lower half 4a and the bottom of the U-shaped recess 12, thereby establishing the form-fit connection of the stabilization elements and a frictional holding force.

As further shown in FIG. 13, the stabilization element 5 has a length with which spans at least one full motion segment. The stabilization element 5 is a rigid stabilization element which can be curved, as shown, and which is anchored in a vertebrae in a usual manner via the bone anchor 8 with receiving portion 9 into which the middle portion of the stabilization element 5 is directly inserted and fixed by tightening the inner screw 13.

The bone anchor 8 shown in FIG. 13 is of the type of a mono-axial bone anchor which means that the receiving portion and a threaded shaft are not pivotably connected to each other.

In the embodiment shown in FIG. 13 the rigid stabilization element 5 has a circular cross-section and is provided at both ends with a connection element 14 shown in FIG. 14. The connection element 14 is rotationally symmetric and comprises a first end 14a and a second end 14b. Adjacent to the first end 14a a circular rib-like projection 15 is provided which is shaped like the rib-like projection 33 of the inner connection element such that, as shown in FIG. 1, the rigid stabilization element 5 can be connected to a flexible stabilization element 2. Adjacent to the second end 14b, the connection element 14 includes a rib-like projection 16, the outer diameter and the shape of which corresponds to the outer diameter and the shape of the rib-like projection 23 of the flexible stabilization element 2 and fits to the inner structure of the outer connection element 4a, 4b. The connection element 14 further comprises on its second end 14b a coaxial blind hole (not shown) for inserting a stabilization element 6 as shown in FIG. 13. The connection element 14 is of the flexible type, i.e. it is made, for example, of a flexible material such as an elastomer, in particular from PCU.

The stabilization element 6 is rigid and has a non-circular cross-section, for example a rectangular cross-section. It may have a projection at its ends to be received in a form fit manner in the connection element 14.

FIGS. 15 and 16 show a variation of the bone anchor, which is in the form of a polyaxial bone screw. It comprises a screw element 8' which is pivotably held in the receiving portion 9'. To fix the angular position of the screw element 8', a pressure element 20 is provided which presses onto the head 8a of the bone anchor 8'. All other parts with the same reference numerals are the same as described already in connection with FIG. 13. The stabilization element 5 shown in FIGS. 15 and 16 is a rigid stabilization element which is anchored by the polyaxial bone screw at its middle portion. This is useful if the stabilization element is intended to cover more than one single motion segment. In such a case conventional polyaxial bone anchors can be used.

Figure 17:
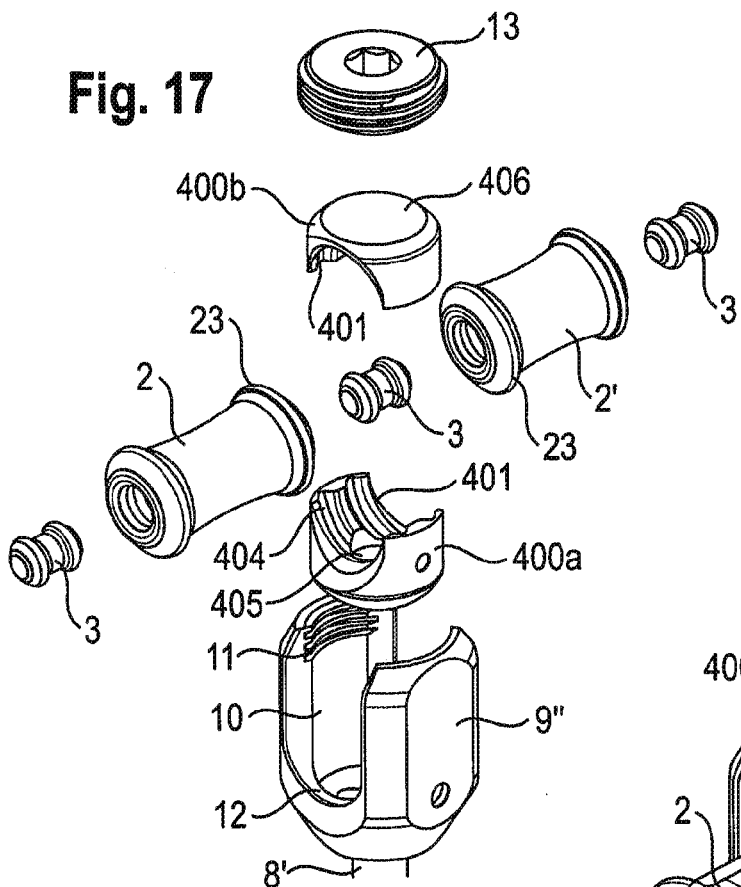
FIG. 17 shows an exploded perspective view of the stabilization system with two different stabilization elements and a bone anchor.
Figure 18:
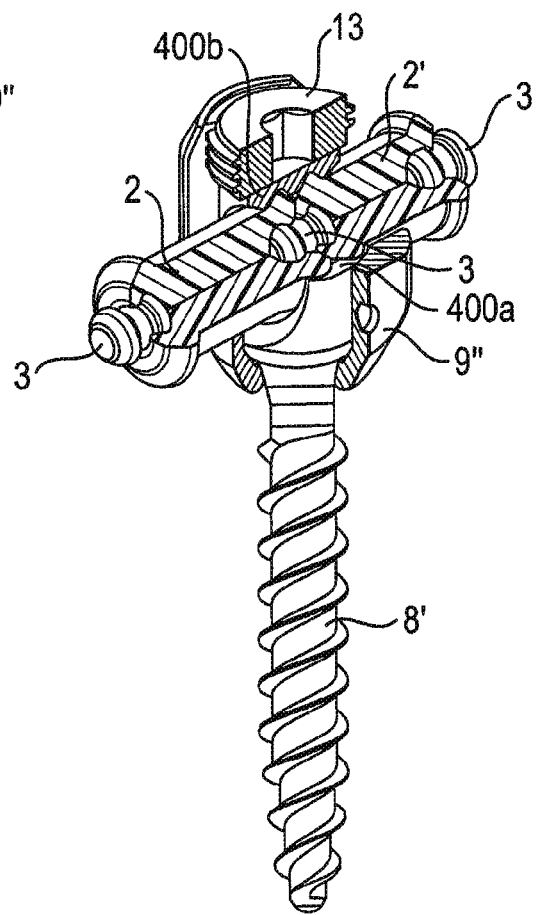
FIG. 18 shows a partially sectional view of the system of FIG. 17 in an assembled and fixed state.

The stabilization system shown in FIGS. 17 and 18 differs from the stabilization system shown in FIGS. 15 and 16 in that the bone anchor is a specifically adapted polyaxial bone anchor to anchor flexible stabilization elements 2, 2'. The screw element 8' is the same as the screw element 8' shown in FIGS. 15 and 16. The receiving part 9'' is also pivotably connected to the screw element and comprises a central bore 10 which tapers at one end to pivotably hold the head 8a of the screw element 8'. Also, like in the embodiment of FIGS. 15 and 16, the U-shaped recess 12 is provided in the receiving part 9'' and an internal thread 11 for screwing-in the inner screw 13. The receiving part 9' has a height which is designed in such a way that an outer connection element 400a, 400b which encompasses the two flexible stabilization elements 2, 2' and the inner connection element 3 can be accommodated therein. The flexible stabilization elements 2, 2' are the same as those shown in FIGS. 2 to 6.

The outer connection element consists of two halves 400a, 400b which have a generally cylindrical shape and a cylinder-segment shaped recess 401 to accommodate the end portions of the flexible stabilization elements between them. Similar to the outer connection element 4a, 4b shown in FIGS. 7 to 9 the outer connection element 400a, 400b includes circular grooves 404 to establish a form-fit connection with the circular ribs 23 of the stabilization elements 2, 2'. The lower half 400a of the outer connection element includes a central bore 405 which allows to access the head 8a of the screw element with a tool. In addition, the lower half of the outer connection element 400a includes opposite to the cylinder segment-shaped recess 401, a substantially spherical recess (not shown) which is adapted to fit onto the head 8a of the screw element 8'. Hence, the function of the lower half 400a of the outer connection element is also the function the pressure element 20 shown in FIG. 15 which exerts pressure onto the head of the screw element to lock the head of the screw element in its angular position. The upper half 400b of the outer connection element has a flat surface 406, for example.

As shown in the assembled state according to FIG. 18, when the inner screw 13 is tightened down, it presses the upper half 400b against the lower half 400a and engages the ends of the flexible elements 2, 2' in a form-fit connection. When the inner screw 13 is finally tightened, the angular position of the screw element with respect to the receiving part and also the connection between the two flexible elements is fixed.

Figure 19:
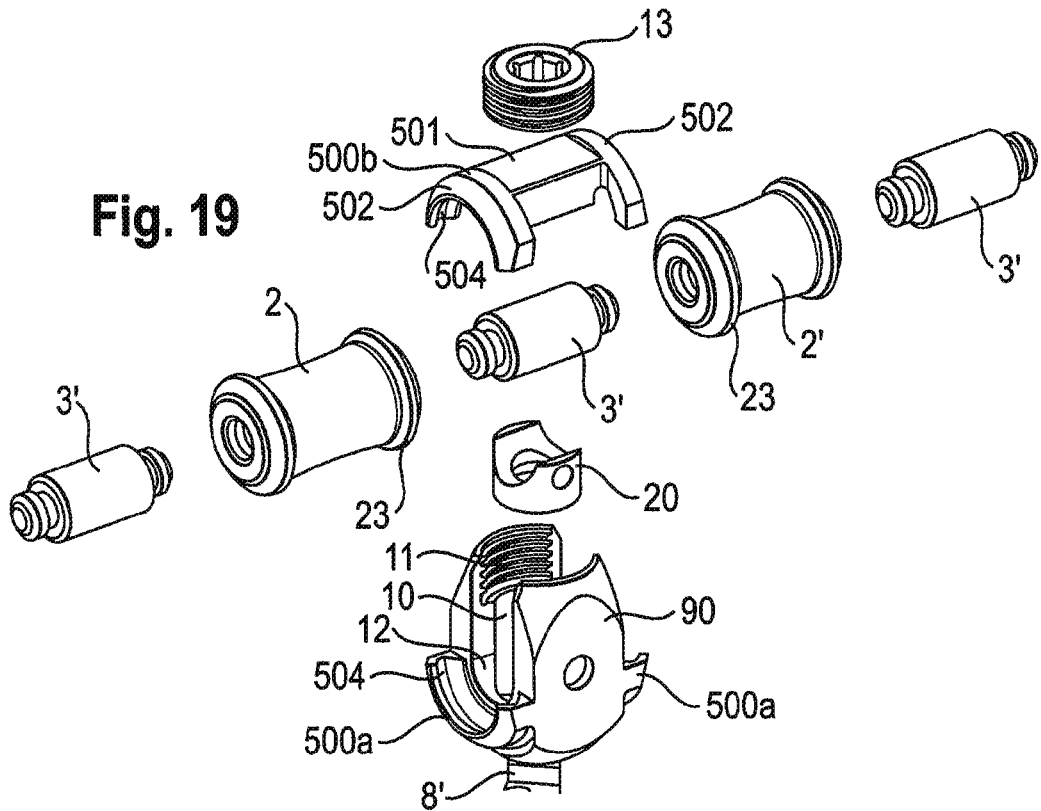
FIG. 19 shows an exploded perspective view of the stabilization system with two stabilization elements and a modified bone anchor.
Figure 20:
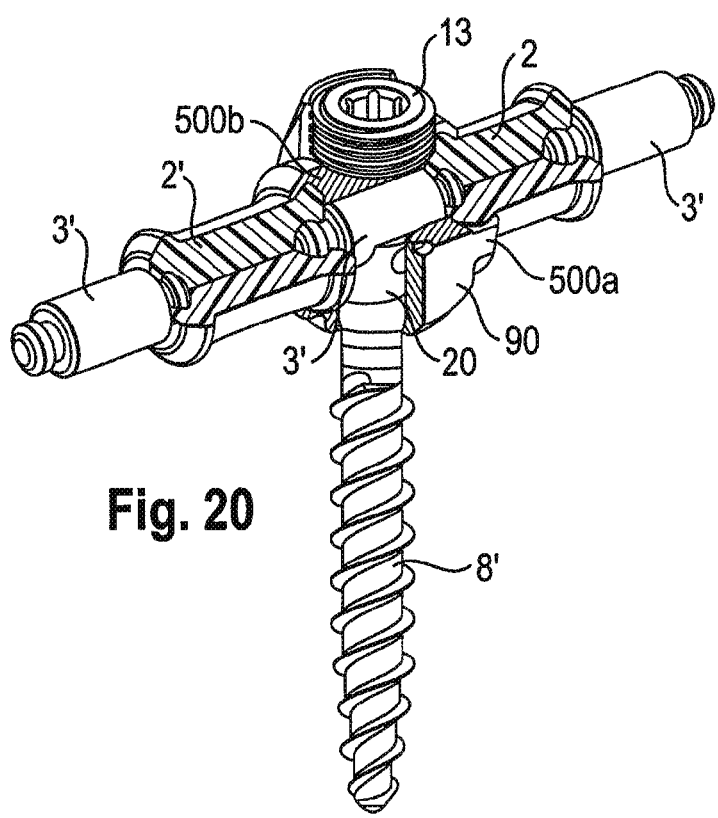
FIG. 20 shows a partially sectional view of the system of FIG. 19 in an assembled and fixed state.

The stabilization system shown in FIGS. 19 and 20 differs from the stabilization system shown in FIGS. 17 and 18 in that the outer connection element 500a, 500b is partly integrated in the receiving portion 90. Also, the inner connection element 3' is adapted to correspond to the outer connection element. As in the previous embodiment the receiving portion 90 is pivotably connected to the screw member 8'. The receiving portion 90 has at both sides of the channel formed by the U-shaped recess 12 a cylinder segment-shaped projection 500a which forms the lower half of the outer connection element. The cylinder segment shaped projection 500a includes as in the previous embodiments circular grooves 504 for the purpose of form-fit connection with the circular rib 23 of the flexible stabilization element 2, 2'. All other portions of the receiving portion 90 are identical to those of the receiving portion 9' of the previous embodiment.

The upper half 500b of the outer connection element is generally cylindrically-shaped with the cylinder axis being parallel to the cylinder axis of the channel formed by the U-shaped recess 12. The upper half 500b comprises a main portion 501 which presses onto the inner connection element 3' and two cylinder segment shaped end portions at both ends which are complementary to the portions 500a at the receiving portion 90 and which have a circular groove 504 adapted to accommodate the circular rib 23 of the flexible stabilization element. The length of the central portion 501 is such that when the upper half 500b is inserted into the receiving portion 90 the end portions 502 extend beyond the U-shaped recess and are located so as to face the portions 500a of the receiving portion. The inner connection element 3' has a prolonged middle portion the length of which is such that the end portions extend beyond the receiving portion 90. In addition, a pressure element 20 which is the conventional pressure element shown in FIG. 15 is provided to lock the position of the screw head 8a.

As shown in FIG. 20 the flexible elements 2, 2' are clamped between the portions 500a and the upper half 500b of the outer connection element. The clamping takes place outside the central portion of the receiving portion 90. In the bore 10 of the receiving portion 90 the rigid inner connection element 3' is clamped. With this design, the flexible stabilization elements can be made shorter than in the previous embodiments. It should be noted that the lower half 500a of the outer connection element needs not to be integrally shaped with the receiving portion 90 it is also conceivable that the pressure element 20 comprises extensions extending beyond the receiving portion.

FIGS. 21 to 23 show modifications of the flexible stabilization element. FIGS. 21a and 21b show a flexible stabilization element 2" which is curved and which has an approximately rectangular cross section. This provides an oriented flexibility, i.e. the element has a higher stiffness in one direction than in another direction. Generally, in the portion between the two ends of the stabilization element the cross-section of the element can be designed such that the desired stiffness or an oriented flexibility is achieved.

FIGS. 22a and 22b show a further modification of the flexible stabilization element 20' which differs in that instead of a single rib-like circular projection a plurality of fine circular ribs 20a' are provided which permit balancing of the length of the stabilization element within the outer connection element 4a, 4b.

FIGS. 23a and 23b show a further modification of the flexible stabilization element 200,200' which differs from the previously described flexible stabilization elements in that a spherical segment-shaped projection 200a the diameter of which increases towards the end is provided. This allows a simple construction of the outer connection element and a free rotational alignment thereof.

Other modifications are conceivable. The end portions of the stabilization elements need not have a circular rib-like projection. Any structure, which can provide a form-fit connection, is suitable. The rigid stabilization elements can be shaped at the ends to be insertable in the blind hole of the flexible stabilization element. The inner connection element may be omitted.

The outer connection elements have to be adapted to the shape of the end portions of the flexible stabilization elements. A particular modification can be that the outer connection elements 4a, 4b are not provided as separate elements but integrated into the bone anchors. In this case, either the bottom of the U-shaped recess and/or the lower portion of the fixation screw 13 has a structure for form-fit engagement. Alternatively, only the upper or the lower structure is integrated into the receiving portion and the complementary other structure is provided in a separate element. Providing the outer connection element as a separate element, has the advantage that existing bone anchors can be used and upgraded with the outer connection element.

Any known bone anchors can be used. The fixation is not restricted to an inner screw as a fixation element.

In operation, the surgeon anchors at least two, usually a plurality of bone anchors in adjacent vertebrae of the portion of the spine which is to be stabilized. Thereafter, the stabilization system is assembled by selecting appropriate flexible and/or rigid stabilization elements and connecting them outside the patient's body. Then the assembled rod-like stabilization system is inserted in such a way that it is fixed in the bone anchors at the connection sites. Finally, the inner screws are tightened to fix the system in the bone anchors.

What is claimed is:

1. A modular stabilization system for the stabilization of the spinal column or other bones comprising:
    a first stabilization element having a longitudinal axis;
    a second stabilization element having a longitudinal axis;
    at least one bone anchor comprising a shaft to be anchored in the bone, a receiving part comprising a recess for receiving at least one of the first stabilization element and the second stabilization element, and a securing device for securing the at least one of the first stabilization element and the second stabilization element in the receiving part when the at least one of the first stabilization element and the second stabilization element is in the receiving part;
    an outer connection element comprising a first part and a second part, at least one of the first part and the second part having a recess configured to be in opposed relation to the other of the first part and the second part to simultaneously receive the first stabilization element and the second stabilization element therein;
    wherein an end portion of the first stabilization element comprises a structure configured to engage with a corresponding structure of at least one of the first part and the second part of the outer connection element to establish a first form-fit connection;
    wherein an end portion of the second stabilization element comprises a structure configured to engage with a corresponding structure of at least one of the first part and the second part of the outer connection element to establish a second form-fit connection; and
    wherein the first and second form-fit connections inhibit movement of the first stabilization element and the second stabilization element away from one another along their longitudinal axes when connection.

2. The system according to claim 1, wherein each of the first part and the second part of the outer connection element comprises said recess, each recess having a first groove, and wherein the structure of the end portion of the first stabilization element comprises a rib-shaped projection configured to engage with the first groove in the first part of the outer connection element and to engage with the first groove in the second part of the outer connection element.

3. The system according to claim 2, wherein each recess of the first part and the second part comprises a second groove, and wherein the structure of the end portion of the second stabilization element comprises a rib-shaped projection configured to engage with the second groove in the first part of the outer connection element and to engage with the second groove in the second part of the outer connection element.

4. The system according to claim 1, wherein at least one of the first part and the second part of the outer connection element is inserted in the receiving part.

5. The system according to claim 1, wherein at least the first stabilization element is flexible.

6. The system according to claim 5, wherein the first stabilization element is made of an elastomer.

7. The system according to claim 5, wherein the second stabilization element is made of a rigid material.

8. The system according to claim 7, wherein the second stabilization element is made of at least one of a bio-compatible metal and a rigid plastic material.

9. The system according to claim 1, wherein the end portion of the first stabilization element also comprises an inner connection element.

10. The system according to claim 9, wherein the inner connection element has a rib-shaped projection that is configured to engage with undercut in a coaxial bore of the first stabilization element.

11. The system according to claim 9, wherein each of the first part and the second part of the outer connection element comprises said recess, each recess having a first groove, and wherein the structure of the end portion of the first stabilization element comprises a rib-shaped projection configured to engage with the first groove in the first part of the outer connection element and to engage with the first groove in the second part of the outer connection element.

12. The system according to claim 11, wherein each recess of the first part and the second part comprises a second groove, and wherein the structure of the end portion of the second stabilization element comprises a rib-shaped projection configured to engage with the second groove in the first part of the outer connection element and to engage with the second groove in the second part of the outer connection element.

13. The system according to claim 1 wherein the stabilization elements are rod-shaped.

14. The system according to claim 1, wherein at least one of the first stabilization element and the second stabilization element is flexible, and wherein a length of the flexible stabilization element is configured such that only one single motion segment of the spinal column can be bridged with the stabilization element.

15. The system according to claim 1, wherein the first part and the second part of the outer connection element comprise two complementary first and second halves.

16. The system according to claim 1, further comprising a clamp engaging the first part of the outer connection element and the second part of the outer connection element to secure the first part to the second part.

17. The system according to claim 1, wherein the receiving part further comprises the first part of the outer connection element.

18. A modular stabilization system for the stabilization of the spinal column or other bones comprising:
a first stabilization element having a longitudinal axis;
a second stabilization element having a longitudinal axis;
at least one bone anchor comprising a shaft to be anchored in the bone, a receiving part for receiving at least one of the first stabilization element and the second stabilization element, and a securing device for securing the at least one of the first stabilization element and the second stabilization element to the receiving part when the at least one of the first stabilization element and the second stabilization element is in the receiving part;
an inner connection element having a first end portion configured to connect to an end portion of the first stabilization element and a second end portion configured to connect to an end portion of the second stabilization element to connect the first stabilization element to the second stabilization element;
an outer connection element comprising a first part and a second part, at least one of the first part and the second part having a recess configured to be in opposed relation to the other of the first part and the second part to simultaneously receive the first stabilization element and the second stabilization element therein;
wherein one of the end portion of the first stabilization element and the first end portion of the inner connection element comprises a first inner structure configured to engage with a corresponding structure of at least one of the first part and the second part of the outer connection element to establish a first form fit connection; and
wherein one of the end portion of the second stabilization element and the second end portion of the inner connection element comprises a second inner structure configured to engage with a corresponding structure of at least one of the first part and the second part of the outer connection element to establish a second form-fit connection; and
wherein the first and the second form-fit connections inhibit movement of the first stabilization element and the second stabilization element away from one another along their longitudinal axes when connected.

19. The system according to claim 18, wherein the first end portion and the second end portion of the inner connection element each has a rib-shaped projection that is configured to engage with a respective undercut in a respective coaxial bore at the end portions of the first stabilization element and the second stabilization element, respectively.

20. The system according to claim 18, wherein at least one of the first part and the second part of the outer connection element is inserted into the receiving part.

21. The system according to claim 18, wherein at least the first stabilization element is flexible.

22. The system according to claim 21, wherein the second stabilization element is made of a rigid material.

23. The system according to claim 22, wherein the second stabilization element is made of at least one of a bio-compatible metal and a rigid plastic material.

24. The system according to claim 18, wherein the first stabilization element is made of an elastomer.

25. The system according to claim 18, wherein the inner connection element is rigid.

26. The system according to claim 18, wherein the first end portion of the inner connection element has a rib-shaped projection that is configured to engage with an undercut in a coaxial bore at the end portion of the first stabilization element.

27. The system according to claim 18 wherein the stabilization elements are rod-shaped.

28. The system according to claim 18, wherein at least one of the first stabilization element and the second stabilization element is flexible, and wherein a length of the flexible stabilization element is configured such that only one single motion segment of the spinal column can be bridged with the stabilization element.

29. The system according to claim 18, wherein the first part and the second part of the outer connection element comprise two complementary first and second halves.

30. The system according to claim 29, further comprising a clamp engaging the first half of the outer connection element and the second half of the outer connection element to secure the first half to the second half.

31. The system according to claim 29, wherein the receiving part further comprises the first half of the outer connection element.

32. The system according to claim 18, wherein the first inner structure comprises a rib-shaped projection, and wherein the corresponding structure of the at least one of the first part and the second part of the outer connection element comprises a groove.

33. The system according to claim 32, wherein the second inner structure comprises a rib-shaped projection, and wherein the corresponding structure of the at least one of the first part and the second part of the outer connection element comprises a groove.

34. A method of attaching a modular stabilization system to a bone or vertebra for the stabilization of the spinal column or other bones, the system comprising a first stabilization element having a longitudinal axis, a second stabilization element having a longitudinal axis, at least one bone anchor comprising a shaft to be anchored in the bone, a receiving part comprising a recess for receiving at least one of the first stabilization element and the second stabilization element, and a securing device for securing the at least one of the first stabilization element and the second stabilization element in the receiving part when the at least one of the first stabilization element and the second stabilization element is in the receiving part, an outer connection element comprising a first part and a second part, at least one of the first part and the second part having a recess configured to be in opposed relation to the other of the first part and the second part to simultaneously receive the first stabilization element and the second stabilization element therein, wherein an end portion of the first stabilization element comprises a structure configured to engage with a corresponding structure of at least one of the first part and the second part of the outer connection element to establish a first form-fit connection, wherein an end portion of the second stabilization element comprises a structure configured to engage with a corresponding structure of at least one of the first part and the second part of the outer connection element to establish a second form-fit connection, wherein the first and second form-fit connections inhibit movement of the first stabilization element and the second stabilization element away from one another along their longitudinal axes when connected, the method comprising:
- attaching the shaft of the bone anchor to a bone or vertebra;
- connecting the outer connection element to the first stabilization element and the second stabilization element; and
- securing at least one of the first stabilization element and the second stabilization element in the receiving part with the securing device.

35. The method of claim 34, wherein after connecting the outer connection element to the first stabilization element and the second stabilization element, the outer connection element is inserted in the receiving part and secured therein with the securing device.

36. The method of claim 34, wherein before connecting the outer connection element to the first stabilization element and the second stabilization element, the first stabilization element and the second stabilization element are connected with an inner connection element.

* * * * *

UNITED STATES PATENT AND TRADEMARK OFFICE
CERTIFICATE OF CORRECTION

PATENT NO. : 8,414,621 B2  
APPLICATION NO. : 12/540267  
DATED : April 9, 2013  
INVENTOR(S) : Lutz Biedermann et al.

Page 1 of 1

It is certified that error appears in the above-identified patent and that said Letters Patent is hereby corrected as shown below:

In the Claims

Column 8, Claim 1, line 45      Delete "connection"  
     Insert -- connected --

Column 9, Claim 10, line 11      After "with"  
     Insert -- an --

Signed and Sealed this  
Tenth Day of June, 2014

Michelle K. Lee  
*Deputy Director of the United States Patent and Trademark Office*